United States Patent
Mayer et al.

(10) Patent No.: US 9,814,231 B2
(45) Date of Patent: Nov. 14, 2017

(54) EMULSIFIABLE CONCENTRATE COMPRISING PESTICIDE, ALKYL LACTATE, FATTY ACID DIALKYLAMIDE AND DIESTER

(71) Applicant: BASF SE, Ludwigshafen (DE)

(72) Inventors: Winfried Mayer, Bubenheim (DE); Juergen Jakob, Roedersheim-Gronau (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/778,813

(22) PCT Filed: Mar. 3, 2014

(86) PCT No.: PCT/EP2014/054098
§ 371 (c)(1),
(2) Date: Sep. 21, 2015

(87) PCT Pub. No.: WO2014/154448
PCT Pub. Date: Oct. 2, 2014

(65) Prior Publication Data
US 2016/0044915 A1    Feb. 18, 2016

(30) Foreign Application Priority Data

Mar. 27, 2013  (EP) .................................... 13161263
Aug. 5, 2013   (EP) .................................... 13179210

(51) Int. Cl.
*A01N 25/02* (2006.01)
*A01N 25/04* (2006.01)
*A01N 43/56* (2006.01)

(52) U.S. Cl.
CPC ............. *A01N 25/02* (2013.01); *A01N 25/04* (2013.01); *A01N 43/56* (2013.01)

(58) Field of Classification Search
CPC .. A01N 43/653; A01N 25/02; A01N 2300/00; A01N 55/00; A01N 37/18
See application file for complete search history.

(56) References Cited

U.S. PATENT DOCUMENTS 5,206,225 A      4/1993  Horstmann et al.
2011/0070278 A1  3/2011  Lopez

FOREIGN PATENT DOCUMENTS

| DE | EP2327302 A1 * | 11/2009 | ............. A01N 25/02 |
| EP | 0 453 899 | 10/1991 | |
| EP | 2 269 451 | 1/2011 | |
| EP | 2 327 302 | 6/2011 | |
| EP | 2 335 480 | 6/2011 | |
| WO | WO 2011/109689 | 9/2011 | |
| WO | WO 2012/069514 | 5/2012 | |
| WO | WO2012/069514 A1 * | 5/2012 | ............. A01N 25/10 |
| WO | WO2012069514 A1 * | 5/2012 | ............. A01N 25/10 |

OTHER PUBLICATIONS

EP2327302A1, filed Nov. 2009, published Jun. 2011, "Merlet et al.", translation accessed Feb. 21, 2017.*
International Search Report dated Apr. 2, 2014, prepared in International Application No. PCT/EP2014/054098.
International Preliminary Report on Patentability dated Sep. 29, 2015, prepared in International Application No. PCT/EP2014/054098.
European Search Report, prepared in corresponding EP Application No. 13161263.2, filed Mar. 27, 2013.

* cited by examiner

*Primary Examiner* — Audrea Buckley
(74) *Attorney, Agent, or Firm* — Brinks Gilson & Lione

(57) ABSTRACT

Subject matter of the present invention is an emulsifiable concentrate comprising a water-insoluble pesticide, a) an alkyl lactate, b) an amide of the formula (I), and c) a diester of the formula (II) as defined below. The invention further relates to a process for the preparation of said concentrate; an emulsion obtainable by mixing water, a water-insoluble pesticide, the components a), b) and c); and to a method for controlling phytopathogenic fungi and/or undesired vegetation and/or undesired attack by insects or mites and/or for regulating the growth of plants, where the concentrate or the emulsion is allowed to act on the respective pests, their environment or on the crop plants to be protected from the respective pests, on the soil and/or on undesired plants and/or on the crop plants and/or their environment.

19 Claims, No Drawings

EMULSIFIABLE CONCENTRATE COMPRISING PESTICIDE, ALKYL LACTATE, FATTY ACID DIALKYLAMIDE AND DIESTER

This application is a National Stage application of International Application No. PCT/EP2014/054098, filed Mar. 3, 2014. This application also claims priority under 35 U.S.C. §119 to European Patent Application No. 13161263.2, filed Mar. 27, 2013, and European Patent Application No. 13179210.3, filed Aug. 5, 2013.

Subject matter of the present invention is an emulsifiable concentrate comprising a water-insoluble pesticide, a) an alkyl lactate, b) an amide of the formula (I), and c) a diester of the formula (II) as defined below. The invention further relates to a process for the preparation of said concentrate; an emulsion obtainable by mixing water, a water-insoluble pesticide, the components a), b) and c); and to a method for controlling phytopathogenic fungi and/or undesired vegetation and/or undesired attack by insects or mites and/or for regulating the growth of plants, where the concentrate or the emulsion is allowed to act on the respective pests, their environment or on the crop plants to be protected from the respective pests, on the soil and/or on undesired plants and/or on the crop plants and/or their environment. The present invention comprises combinations of preferred features with other preferred features.

Emulsifiable concentrates (also referred to as EC) are widely used formulations in crop protection. The disadvantage of the known emulsifiable concentrates is the poor cold stability, the pronounced tendency to crystallize and the low pesticide concentration.

It was an object of the present invention to provide an emulsifiable concentrate which overcomes these disadvantages.

The object was achieved by an an emulsifiable concentrate comprising a water-insoluble pesticide,
a) an alkyl lactate,
b) an amide of the formula (I)

  (I)

where $R^1$ is $C_5$-$C_{19}$-alkyl and $R^2$ is $C_1$-$C_4$-alkyl, and
c) a diester of the formula (II)

  (II)

where $R^3$ is $C_1$-$C_8$-alkyl and $R^4$ is $C_1$-$C_{10}$-alkanediyl or $C_2$-$C_{10}$-alkenediyl.

Usually, an emulsifiable concentrate is taken to mean compositions which form an oil-in-water emulsion upon mixing with water (e.g. in a weight ratio of 1 part concentrate to 99 parts water). The mixing of the emulsifiable concentrate with water may be done at 5 to 50° C., typically at ambient temperature such as 25° C. The emulsion usually arises spontaneously. In another form the emulsion usually arises spontaneously upon mixing. The resulting emulsion may have an average droplet size of more than 0.1 μm, preferably more than 0.5 μm, in particular more than 0.8 μm, and most preferred more than 1.1 μm. The average droplet size may be determined by laser diffraction, e.g. with a Malvern Mastersizer 2000.

The concentrate is preferably present as a homogeneous solution. It is usually virtually free from dispersed particles.

Suitable alkyl lactates are aliphatic $C_1$-$C_{18}$-alkyl lactates (in particular $C_6$-$C_{10}$-alkyl lactates), which may be linear or branched. Examples are cyclohexyl lactate, 2-ethylhexyl lactate, 2-methylcyclohexyl lactate, heptyl lactate, octyl lactate, or mixtures of these. Especially preferred is 2-ethylhexyl lactate. The alkyl lactates can be present in the form of D- and/or L-lactates, with the L-lactates being preferred.

The concentrate can comprise at least 5% by weight, preferably at least 15% by weight and in particular at least 22% by weight of alkyl lactate (such as 2-ethylhexyl lactate). The concentrate can comprise not more than 65% by weight, preferably not more than 50% by weight and in particular not more than 35% by weight of the alkyl lactate.

Preferred amides of the formula (I) are those in which $R^1$ is $C_7$-$C_{11}$-alkyl and $R^2$ is methyl. Especially preferred amides of the formula (I) are those in which $R^1$ is $C_7$-$C_9$-alkyl and $R^2$ is methyl. In particular, $R^1$ is n-nonyl and $R^2$ is methyl.

Mixtures of amides of the formula (I) are also possible, for example mixtures where $R^1$ is $C_7$-$C_{11}$-alkyl and $R^2$ is methyl. Mixtures of amides of the formula (I) comprise in most cases two amides of the formula (I) in an amount of in each case at least 30% by weight (preferably at least 40% by weight) based on the total amount of amides of the formula (I).

The concentrate can comprise not more than 55% by weight, preferably not more than 35% by weight and in particular not more than 25% by weight of amide of the formula (I). The concentrate can comprise at least 3% by weight, preferably at least 5% by weight and in particular at least 10% by weight of amide of the formula (I).

Preferred diesters of the formula (II) are those where $R^3$ is $C_1$-$C_4$-alkyl and $R^4$ is $C_3$-$C_6$-alkanediyl or $C_2$-$C_{10}$-alkenediyl. Especially preferred diesters of the formula (II) are those where $R^3$ is $C_1$-$C_2$-alkyl and $R^4$ is butanediyl. A particularly suitable diester is dimethyl adipate.

The concentrate can comprise not more than 50% by weight, preferably not more than 35% by weight and in particular not more than 20% by weight of diester of the formula (II). The concentrate can comprise at least 3% by weight, preferably at least 5% by weight and in particular at least 10% by weight of diester of the formula (II).

The weight ratio of the alkyl lactate to the amide of the formula (I) may be in the range from 1:20 to 10:1, preferably from 1:10 to 4:1, more preferably from 1:6 to 1.5:1, and in particular from 1:4 to 1:1.2. In another form the weight ratio of the alkyl lactate to the amide of the formula (I) may be in the range from 1:10 to 20:1, preferably from 1:5 to 5:1, more preferably from 1:3.5 to 3.5:1, and in particular from 1:2 to 2:1.

The concentrate may further comprise benzyl alcohol in addition to the aforementioned solvents a), b) and c). The concentrate can comprise not more than 30% by weight, preferably not more than 10% by weight and in particular not more than 7% by weight of benzyl alcohol. The concentrate can comprise at least 0.5% by weight, preferably at least 1.5% by weight and in particular at least 3% by weight of benzyl alcohol.

The concentrate may further comprise dimethyl sulfoxide (DMSO) in addition to the aforementioned solvents a), b) and c). The concentrate can comprise not more than 20% by weight, preferably not more than 10% by weight and in particular not more than 3% by weight of dimethyl sulfoxide. The concentrate can comprise at least 0.1% by weight, preferably at least 0.5% by weight and in particular at least 1% by weight of DMSO.

The concentrate may further comprise benzyl alcohol and dimethyl sulfoxide (DMSO) in addition to the aforementioned solvents a), b) and c).

The amounts of these components a), b), c) and optionally benzyl alcohol and optionally DMSO add up to a sum of 5 to 95% by weight, preferably 40 to 90% by weight, and in particular 55 to 85% by weight.

The concentrate can comprise from 10 to 50% by weight of the alkyl lactate (e.g. 2-ethylhexyl lactate), 2 to 35% by weight of the amide of the formula (I) (e.g. in which $R^1$ is $C_7$-$C_{11}$-alkyl and $R^2$ is methyl), 2 to 30% by weight of the diester of the formula (II) (e.g. dimethyl adipate), optionally 1 to 25% by weight of the benzyl alcohol, and optionally 0.1 to 10% by weight of DMSO, wherein the amounts of these components adds up to a sum of 40 to 90% by weight.

Preferably, the concentrate can comprise from 15 to 40% by weight of the alkyl lactate (e.g. 2-ethylhexyl lactate), 5 to 30% by weight of the amide of the formula (I) (e.g. in which $R^1$ is $C_7$-$C_{11}$-alkyl and $R^2$ is methyl), 5 to 25% by weight of the diester of the formula (II) (e.g. dimethyl adipate), optionally 1 to 20% by weight of the benzyl alcohol, and optionally 0.1 to 5% by weight of DMSO, wherein the amounts of these components adds up to a sum of 40 to 90% by weight.

In particular, the concentrate can comprise from 20 to 35% by weight of the alkyl lactate (e.g. 2-ethylhexyl lactate), 10 to 25% by weight of the amide of the formula (I) (e.g. in which $R^1$ is $C_7$-$C_{11}$-alkyl and $R^2$ is methyl), 10 to 20% by weight of the diester of the formula (II) (e.g. dimethyl adipate), optionally 3 to 15% by weight of the benzyl alcohol, and optionally 0.3 to 3% by weight of DMSO, wherein the amounts of these components adds up to a sum of 40 to 90% by weight.

In most cases, the concentrate is free from water. In another form, the concentrate is essentially free from water. It can comprise not more than 3% by weight, preferably not more than 1% by weight and in particular not more than 0.5% by weight of water. In special form, the concentrate may comprise not more than 0.3% by weight and in particular not more than 0.1% by weight of water.

The concentrate may comprise further solvents (e.g. the organic solvents listed below) in addition the components a), b), c) benzyl alcohol and DMSO. The concentrate can comprise not more than 30% by weight, preferably not more than 10% by weight and in particular not more than 1% by weight of the further solvents.

The term pesticides refers to at least one active substance selected from the group of the fungicides, insecticides, nematicides, herbicides, safeners and/or growth regulators. Preferred pesticides are fungicides, insecticides, herbicides and growth regulators. Especially preferred pesticides are fungicides. Mixtures of pesticides from two or more of the abovementioned classes may also be used. The skilled worker is familiar with such pesticides, which can be found, for example, in Pesticide Manual, 15th Ed. (2009), The British Crop Protection Council, London. The following pesticides are suitable, by way of example (pesticides A) to K) are fungicides):

A) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate inhibitors of complex II (e.g. carboxamides): benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl) pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S3R)-3-(2-chlorophenyl)-2-(2,4-difluorophenyl)-oxiranylmethyl]-5-thiocyanato-1H-[1,2,4]triazole, 2-[rel-(2S3R)-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic Acid Synthesis Inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of Cell Division and Cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

E) Inhibitors of Amino Acid and Protein Synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors
MAP/histidine kinase inhibitors: fluoroimid, iprodione, procymidone, vinclozolin, fenpiclonil, fludioxonil;
G protein inhibitors: quinoxyfen;

G) Lipid and Membrane Synthesis Inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acids: propamocarb, propamocarb-hydrochlorid;
fatty acid amide hydrolase inhibitors: oxathiapiprolin;

H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell Wall Synthesis Inhibitors
inhibitors of glucan synthesis: validamycin, polyoxin B;
melanin synthesis inhibitors: pyroquilon, tricyclazole, carpropamid, dicyclomet, fenoxanil;

J) Plant Defence Inducers
acibenzolar-S-methyl, probenazole, isotianil, tiadinil, prohexadione-calcium; phosphonates: fosetyl, fosetyl-aluminum, phosphorous acid and its salts;

K) Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

M) Growth Regulators
abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides
acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
amino acid derivatives: bilanafos, glyphosate, glufosinate, sulfosate;
aryloxyphenoxypropionates: clodinafop, cyhalofop-butyl, fenoxaprop, fluazifop, haloxyfop, metamifop, propaquizafop, quizalofop, quizalofop-P-tefuryl;
Bipyridyls: diquat, paraquat;
(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones: butroxydim, clethodim, cycloxydim, profoxydim, sethoxydim, tepraloxydim, tralkoxydim;
dinitroanilines: benfluralin, ethalfluralin, oryzalin, pendimethalin, prodiamine, trifluralin;
diphenyl ethers: acifluorfen, aclonifen, bifenox, diclofop, ethoxyfen, fomesafen, lactofen, oxyfluorfen;
hydroxybenzonitriles: bomoxynil, dichlobenil, ioxynil;
imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;
pyrazines: chloridazon, flufenpyr-ethyl, fluthiacet, norflurazon, pyridate;
pyridines: aminopyralid, clopyralid, diflufenican, dithiopyr, fluridone, fluroxypyr, picloram, picolinafen, thiazopyr;
sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;
triazines: ametryn, atrazine, cyanazine, dimethametryn, ethiozin, hexazinone, metamitron, metribuzin, prometryn, simazine, terbuthylazine, terbutryn, triaziflam;
ureas: chlorotoluron, daimuron, diuron, fluometuron, isoproturon, linuron, metha-benzthiazuron, tebuthiuron;
other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, Drechslera monoceras, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethyl-amino-2-fluoro-phenyl)-pyridine-2-carboxylic acid methyl ester.

(O) Insecticides
organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthon, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;
GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
macrocyclic lactone insecticides: abamectin, emamectin, milbemectin, lepimectin, spinosad, spinetoram;
mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide, propargite;
moulting disruptor compounds: cryomazine;
mixed function oxidase inhibitors: piperonyl butoxide;
sodium channel blockers: indoxacarb, metaflumizone;
ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyllambda-4-sulfanylidene)carbamoyl]-phenyl]-2-(3-chloro-2-pyridyl)-5-(trifluoromethyl)pyrazole-3-carboxamide; others: benclothiaz, bifenazate, cartap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester.

The pesticide is water-insoluble. Usually, it is soluble in water to not more than 1 g/l, preferably not more than 200 mg/l and in particular to not more than 50 mg/l at 25° C. Examples of water-insoluble pesticides are fluxapyroxad. Using simple preliminary experiments, the skilled worker can select a pesticide with a suitable water-solubility from the above pesticide list.

The pesticide can have a melting point of more than 40° C., preferably more than 70° C. and in particular more than 90° C.

The pesticide is preferably present in the concentrate in dissolved form. Using simple preliminary experiments, the skilled worker can select, from the above pesticide list, a pesticide with a suitable solubility.

In addition to the water-insoluble pesticide, the concentrate can comprise one or more further pesticides. The further pesticide is preferably water-insoluble. Usually, it is soluble in water to not more than 1 g/l, preferably not more than 200 mg/l and in particular not more than 50 mg/l at 25° C. Using simple preliminary experiments, the skilled worker can select a pesticide with a suitable water-solubility from the above pesticide list. In an especially preferred form, the concentrate does not comprise any further pesticide. In another especially preferred form, the further pesticide is epoxiconazol.

In a preferred form the concentrate comprises the water insoluble pesticide fluxapyroxad and optionally a further pesticide, which is water insoluble (e.g. epoxiconazol).

The concentrate may comprise from 0.1 to 60% by weight, preferably from 1 to 25% by weight, in particular from 5 to 15% by weight, of pesticide, the basis being the total of all the pesticides present in the concentrate.

The emulsifiable concentrate can furthermore comprise auxiliaries conventionally used for crop protection products. Suitable auxiliaries are solvents, liquid carriers, surfactants, dispersants, emulsifiers, wetters, adjuvants, solubilizers, penetrants, protective colloids, stickers, thickeners, bactericides, antifreeze agents, antifoam agents, colorants, adhesives and binders.

Suitable solvents and liquid carriers are organic solvents such as mineral oil fractions with medium to high boiling point, for example kerosene, diesel oil; oils of vegetable or animal origin; aliphatic, cyclic and aromatic hydrocarbons, for example toluene, paraffin, tetrahydro-naphthalene, alkylated naphthalenes; alcohols, for example ethanol, propanol, butanol, cyclohexanol; glycols; ketones, for example cyclohexanone; esters, for example carbonates, fatty acid esters, gamma-butyrolactone; fatty acids; phosphonates; amines; amides, for example N-methylpyrrolidone; and their mixtures.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetrant, protective colloid, or auxiliary. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates. Preferred anionic surfactants are sulfates and sulfonates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate. Preferred nonionic surfactants are alkoxylates. Nonionic surfactants such as alkoxylates may also be employed as adjuvants.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds which have negligible or even no pesticidal activity themselves, and which improve the biological performance of the compound I on the target. Examples are surfactants, mineral or vegetable oils, and other auxiliaries. Further examples are listed by Knowles, Adjuvants and Additives, Agrow Reports DS256, T&F Informa UK, 2006, chapter 5.

Suitable bactericides are bronopol and isothiazolinone derivatives such as alkylisothiazolinones and benzisothiazolinones. Suitable antifreeze agents are ethylene glycol, propylene glycol, urea and glycerol. Suitable antifoam agents are silicones, long-chain alcohols, and salts of fatty acids. Suitable colorants (e.g. in red, blue, or green) are pigments which are sparingly soluble in water, and water-soluble dyes. Examples are inorganic colorants (e.g. iron oxide, titanium oxide, iron hexacyanoferrate) and organic colorants (e.g. alizarin, azo and phthalocyanine colorants).

The concentrate preferably comprises at least one anionic surfactant. The concentrate usually comprises not less than 0.5% by weight of anionic surfactants, preferably not less than 2% by weight and in particular not less than 3% by weight. The composition can comprise not more than 30% by weight of anionic surfactants, preferably not more than 15% by weight and in particular not more than 10% by weight.

The concentrate preferably comprises at least one nonionic surfactant (such as alkoxylates). The concentrate usually comprises not less than 1% by weight of nonionic surfactants, preferably not less than 5% by weight and in particular not less than 10% by weight. The composition can comprise not more than 65% by weight of nonionic surfactants, preferably not more than 45% by weight and in particular not more than 35% by weight.

In a preferred form, the concentrate preferably comprises at least one alkoxylate, in particular an alkoxylated $C_6$-$C_{22}$-alcohol. The concentrate usually comprises not less than 2% by weight of alkoxylates (in particular an alkoxylated $C_6$-$C_{22}$-alcohol), preferably not less than 7% by weight and in particular not less than 10% by weight.

Preferably, the concentrate comprises a nonionic surfactant (such as alkoxylates) and an anionic surfactant (such as sulfates or sulfonates).

The invention furthermore relates to a process for the preparation of the emulsifiable concentrate according to the invention by mixing the water-insoluble pesticide, the alkyl lactate, the amide of the formula (I), and the diester of the formula (II).

The invention furthermore relates to an emulsion obtainable (preferably obtained) by mixing water, the water-insoluble pesticide, the components a), b) and c) according to the invention, optionally benzyl alcohol, and optionally dimethyl sulfoxide. The emulsion normally arises spontaneously upon mixing. In most cases, the emulsion is an oil-in-water emulsion. The mixing ratio of water to concentrate can be in the range of from 1000 to 1 up to 1 to 1, preferably 200 to 1 up to 3 to 1.

The invention furthermore relates to a method for controlling phytopathogenic fungi and/or undesired vegetation and/or undesired attack by insects or mites and/or for regulating the growth of plants, where the concentrate according to the invention or the emulsion according to the invention is allowed to act on the respective pests, their environment or on the crop plants to be protected from the respective pests, on the soil and/or on undesired plants and/or on the crop plants and/or their environment. In general, the therapeutic treatment of humans and animals is excluded from the method for controlling phytopathogenic fungi and/or undesired vegetation and/or undesired attack by insects or mites and/or for regulating the growth of plants.

When employed in crop protection, the application rates of the pesticides amount to from 0.001 to 2 kg per ha, preferably from 0.005 to 2 kg per ha, especially preferably from 0.05 to 0.9 kg per ha and in particular from 0.1 to 0.75 kg per ha, depending on the nature of the desired effect. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kg of plant propagation material (preferably seed) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizers or micronutrients and further pesticides (for example herbicides, insecticides, fungicides, growth regulators, safeners) may be added to the emulsion in the form of a premix or optionally only shortly before use (tank mix). These agents can be admixed to the compositions according to the invention at a weight ratio of from 1:100 to 100:1, preferably from 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

Advantages of the present invention are, inter alia, that the concentrate is highly stable to low temperatures (e.g. even below 0° C.); that the pesticide does not precipitate, cream or crystallize in the concentrate at low temperatures (e.g. even below 0° C.); that the pesticide does not precipitate, cream or crystallize in the emulsion obtained from the concentrate, e.g. at low temperatures (e.g. even below 0° C.); that high pesticide concentrations in the concentrate can be employed; that an emulsion forms spontaneously upon dilution of the concentrate with water; that the concentrate is capable of being stored over prolonged periods; that the concentrate does not require the presence of water (e.g. because it might freeze below 0° C. or would favor bacterial growth during storage); that the concentrate forms a stable emulsion upon dilution with water; that adjuvants (such as alcohol alkoxylates) can be included in the concentrate formulations; that the pesticide does in the emulsion obtained from the concentrate does not clogg any spraying filters or nozzles, e.g. at low temperatures, or when diluted with hard water.

The examples which follow illustrate the invention without imposing any limitation.

EXAMPLES

DMA: dimethyl adipate
BenzOH: benzyl alcohol
Amid: N,N-dimethyldecanamide
NS1: nonionic surfactant, liquid ethoxylated polyalkylarylphenol, HLB 12-13.
NS2: nonionic surfactant, liquid alkoxylated fatty alcohol, surface tension (1 g/l, 23° C.) 28-30 mN/m; Brookfield viscosity (23° C.) 70-80 mPas.
NS3: nonionic surfactant, liquid ethoxylated tristyrylphenol.
AS1: calcium alkylbenzenesulfonate, 40% by weight in aromatic solvent.

Examples 1: Preparation of Emulsifiable Concentrates (EC)

The emulsifiable concentrates of fluxapyroxad (in each case 62.5 g/l) were prepared by mixing the components and making up to 1.0 l with (S)-2-ethylhexyl lactate. The compositions are summarized in Table 1.

TABLE 1

| | Composition (all data in g/l) | | | | | | | |
|---|---|---|---|---|---|---|---|---|
| Example | Amid | DMA | BenzOH | DMSO | AS1 | NS1 | NS2 | NS3 |
| 1 | 200 | 150 | 50 | 15 | 25 | 25 | 150 | 25 |
| Comp-1 | — | 150 | 200 | 60 | 50 | 50 | 150 | 50 |

Example 2: Clogging Test

The test below was used to investigate whether the emulsifiable concentrates, following dilution with water to a sprayable concentration, can be used in standard sprayers without clogging the filters of the spraying machine or the spraying nozzles.

The EC of Example 1 or the comparative Example Comp-1 was diluted with hard water (CIPAC D) to prepare 1000 ml of an oil-in-water emulsion containing 1 wt % of said EC. This emulsion was cycled for 60 min through a cartridge with a metal sieve (150 μm) and a pumping rate of 180 l per hour. During the test, the temperature was kept constant at about 10° C. in order to simulate cold well water.

Afterwards the metal sieve was visually inspected for residues. When using the EC from Example 1 no residue such as crystals were found. When using the EC from the comparative Example Comp-1 clearly crystals and residue were found.

We claim:

1. An emulsifiable concentrate comprising a water-insoluble pesticide selected from the group consisting of benodanil, benzovindiflupyr, bixafen, boscalid, carboxin, fenfuram, fluopyram, 5 flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl) pyrazole-4-carboxamide, 3-(trifluoromethyl)-1-methyl-N-(1,1,3-trimethyl-indan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide,
   a) an alkyl lactate,
   b) an amide of the formula (I)

$$R^1-C(O)N(R^2)_2 \quad (I)$$

where $R^1$ is $C_5$-$C_{19}$-alkyl and $R^2$ is $C_1$-$C_4$-alkyl, and
   c) a diester of the formula (II)

$$R^3-O(O)C-R^4-C(O)O-R^3 \quad (II)$$

where $R^3$ is $C_1$-$C_2$ alkyl and $R^4$ is butanediyl.

2. The concentrate according to claim 1, comprising at least 5% by weight of the amide of the formula (I).

3. The concentrate according to claim 1, comprising at least 15% by weight of the alkyl lactate.

4. The concentrate according to claim 1, comprising at least 5% by weight of the diester of the formula (II).

5. The concentrate according to claim 1, comprising benzyl alcohol.

6. The concentrate according to claim 1, comprising not more than 30% by weight of benzyl alcohol.

7. The concentrate according to claim 1, comprising dimethyl sulfoxide.

8. The concentrate according to claim 1, comprising not more than 10% by weight of dimethyl sulfoxide.

9. The concentrate according to claim 1, comprising from 15 to 40% by weight of the alkyl lactate, 5 to 30% by weight of the amide of the formula (I), 5 to 25% by weight of the diester of the formula (II), optionally 1 to 20% by weight of the benzyl alcohol, and optionally 0.1 to 5% by weight of DMSO, wherein the amounts of these components add up to a sum of 40 to 90% by weight.

10. The concentrate according to claim 1, wherein the alkyl lactate is 2-ethylhexyl lactate.

11. The concentrate according to claim 1, wherein $R^1$ is n-nonyl and $R^2$ is methyl.

12. The concentrate according to claim 1, wherein the concentrate is present as a homogeneous solution.

13. A process for the preparation of the concentrate according to claim 1 by mixing the water-insoluble pesticide, the alkyl lactate, the amide of the formula (I), the diester of the formula (II), optionally benzyl alcohol, and optionally dimethyl sulfoxide.

14. An emulsion obtainable by mixing water, a water-insoluble pesticide, an alkyl lactate as defined in claim 1, an amide of the formula (I) as defined in any of claim 1, a diester of the formula (II) as defined optionally benzyl alcohol, and optionally dimethyl sulfoxide.

15. A method for controlling phytopathogenic fungi and/or undesired vegetation and/or undesired attack by insects or mites and/or for regulating the growth of plants, comprising applying the concentrate according to claim 1 on the fungi, insects or mites, their environment or on crop plants to be protected from the fungi, insects or mites, on the soil and/or on undesired plants and/or on the crop plants and/or their environment.

16. A method for controlling phytopathogenic fungi and/or undesired vegetation and/or undesired attack by insects or mites and/or for regulating the growth of plants, comprising applying the emulsion according to claim 14 on the fungi, insects or mites, their environment or on crop plants to be protected from the fungi, insects or mites, on the soil and/or on undesired plants and/or on the crop plants and/or their environment.

17. The method of claim 15, wherein the concentrate comprises at least 5% by weight of the amide of the formula (I).

18. The method of claim 15, wherein the concentrate comprises from 15 to 40% by weight of the alkyl lactate, 5 to 30% by weight of the amide of the formula (I), 5 to 25% by weight of the diester of the formula (II), optionally 1 to 20% by weight of the benzyl alcohol, and optionally 0.1 to 5% by weight of DMSO, wherein the amounts of these components add up to a sum of 40 to 90% by weight.

19. The method of claim 15, wherein the concentrate comprises at least 5% by weight of the diester of the formula (II).

* * * * *